United States Patent [19]

White

[11] 4,193,938

[45] Mar. 18, 1980

[54] EXTRACTION OF PHENYLENEDIAMINE FROM AQUEOUS ALKALINE SOLUTION

[75] Inventor: Preston S. White, Corpus Christi, Tex.

[73] Assignee: PPG Industries, Inc., Pittsburgh, Pa.

[21] Appl. No.: 884,522

[22] Filed: Mar. 8, 1978

[51] Int. Cl.[2] .............................................. C07C 85/26

[52] U.S. Cl. ...................................... 260/582; 260/705

[58] Field of Search ......................... 260/582, 581, 578

[56] References Cited

U.S. PATENT DOCUMENTS

| | | | |
|---|---|---|---|
| 2,385,504 | 9/1945 | Goulding | 260/582 |
| 3,433,788 | 3/1969 | Somekh et al. | 260/582 X |
| 3,686,314 | 8/1972 | Bacha et al. | 260/582 |

FOREIGN PATENT DOCUMENTS

| | | | |
|---|---|---|---|
| 52-95615 | 8/1977 | Japan | 260/582 |
| 52-95616 | 8/1977 | Japan | 260/582 |
| 52-95617 | 8/1977 | Japan | 260/582 |
| 3875 | of 1908 | United Kingdom | 260/581 |

OTHER PUBLICATIONS

Quick, "J. Am. Chem. Soc.", vol. 20, pp. 1033–1042 (1920).

*Primary Examiner*—John Doll
*Attorney, Agent, or Firm*—Edward J. Whitfield

[57] ABSTRACT

Phenylenediamine is obtained in high yield and in high purity from an aqueous alkaline solution of phenylenediamine by liquid-liquid extraction of said solution with a $C_1$ chlorinated solvent.

5 Claims, No Drawings

EXTRACTION OF PHENYLENEDIAMINE FROM AQUEOUS ALKALINE SOLUTION

BACKGROUND OF THE INVENTION

This invention relates to the preparation of phenylenediamines and in particular p-phenylenediamine which is used, for example, in the production of aromatic polyamide-based fiber reinforcing materials.

The preparation of phenylenediamines by the ammonolysis of chlorobenzenes in the presence of a copper catalyst is well known to the art and is described, for example, in British Patent No. 3875 and Jour. Am. Chem. Soc., Vol. 20, pp. 1033–1042 (1920). Although satisfactory conversion of dichlorobenzene to phenylenediamine is typically obtained, the phenylenediamine is difficult to isolate from the reaction mixture and unsatisfactory low yields of a relatively impure product are obtained if, for example, the reaction mixture is simply dehydrated. The phenylenediamine may be separated in the form of its hydrochloride salt, however, difficulties are also encountered in converting the salt form to the free amine.

Japanese patent application Ser. No. 011,327, published Aug. 11, 1977, describes extracting free phenylenediamine from a crude aqueous alkaline ammonolysis reaction mixture with $C_3$ and $C_4$ aliphatic alcohols. However, since these alcohols are appreciably water soluble and tend to form azeotropic mixtures with aqueous solutions, it is doubtful whether substantially complete recovery of phenylenediamine product could be obtained from the extract without the expedient of, for example, azeotropic distillation.

SUMMARY OF THE INVENTION

Phenylenediamine is substantially completely recovered from an aqueous alkaline phenylenediamine solution by liquid-liquid extraction using a $C_1$ chlorinated solvent as the extractant.

DESCRIPTION OF THE INVENTION

In accordance with this invention, it has been found that methylene chloride is uniquely suited for use in extracting phenylenediamine from an aqueous alkaline phenylenediamine solution making possible substantially complete recovery of phenylenediamine from the aqueous alkaline phenylenediamine solution. In addition to methylene chloride, it is also contemplated that other $C_1$ chlorinated solvents, namely, chloroform and carbon tetrachloride, would be of use in the practice of the invention since these substances also possess the desirable properties of methylene chloride, i.e., non-oxidizing, non-acidic, low boiling point and low water solubility.

The invention is particularly suited to the extraction of p-phenylenediamine from aqueous alkaline solutions but is equally applicable to extracting other phenylenediamine isomers, such as o-phenylenediamine and m-phenylenediamine from aqueous alkaline solutions.

Aqueous alkaline solutions of phenylenediamine are typically obtained in the known process of preparing phenylenediamine by the ammonolysis of the corresponding dichlorobenzene wherein dichlorobenzene is reacted with an aqueous ammonia solution at a temperature of about 150° C. to about 250° C. in the presence of a copper catalyst. The reaction should be conducted in the substantial absence of oxygen since phenylenediamines are quite sensitive to oxygen and rapidly decomposes in the presence thereof. Sufficient aqueous ammonia solution is typically used to furnish from about 5 to about 20 moles of anhydrous ammonia per mole of dichlorobenzene, although the precise molar ratio is not particularly critical.

The reaction is conducted at an elevated pressure of from about 500 psig to about 1500 psig, preferably from about 600 psig to 700 psig for a time sufficient to effect the desired degree of conversion of the dichlorobenzene, typically from about 5 to 20 hours and usually about 8 to 12 hours.

Copper or any copper-containing compound may be used to catalyze the reaction. Copper salts such as, for example, cuprous iodide (CuI), cuprous chloride (CuCl), cupric chloride ($CuCl_2$), and cupric sulphate ($CuSO_4$) are preferred. Cuprous ion has been found to be more catalytically active than cupric ion and it is believed that cupric ion becomes catalytically active upon reduction to the cuprous state under reaction conditions. Catalyst concentration is not particularly critical but sufficient copper-containing compound is typically used so as to provide a concentration of from about 0.05 mole to about 0.5 mole of cuprous-copper per mole of dichlorobenzene, usually from about 0.1 mole to about 0.3 mole of cuprous-copper per mole of dichlorobenzene.

At the completion of the reaction, the reaction mixture is typically cooled to below about 50° C. and an oxygen scavenging compound such as sodium hydrosulfite is added to stabilize the crude phenylenediamine against oxidation. The reaction mixture is adjusted to a pH greater than 8.3 and usually to a pH of between 11 and 13 with an alkali metal hydroxide such as sodium hydroxide or potassium hydroxide. Caustic treatment converts the phenylenediamine from its hydrochloride salt to the free form, liberates ammonia from ammonium chloride, and enables the recovery of the copper catalyst as insoluble copper hydroxide which can be readily separated from the reaction mixture by, for example, filtration. Liberated ammonia may be removed by subjecting the reaction mixture to, for example, vacuum flashing.

After removal of liberated ammonia and separation of the copper hydroxide, the aqueous alkaline solution is extracted with $C_1$ chlorinated solvent at a temperature of below about 100° C., preferably from about ambient temperature to about 80° C. and preferably at atmospheric pressure for a time sufficient to extract substantially all of the phenylenediamine from the aqueous alkaline solution. If the extraction is conducted at a temperature above the boiling point of the solvent, sufficient pressure would be required to maintain the liquid phase. In any event, too high a temperature, i.e., in excess of about 100° C., should be avoided to minimize thermal decomposition of the phenylenediamine.

From about 20 percent to about 100 percent by volume of solvent based on the volume of aqueous alkaline solution is typically used for extraction. Depending on conditions and the relative volumes of solvent and aqueous alkaline solution, extraction time typically varies from about 4 to 24 hours, usually from about 6 to 12 hours in order to extract substantially all of the phenylenediamine from the aqueous alkaline solution.

After the extraction is completed, the organic phase containing the phenylenediamine is separated from the aqueous alkaline phase. The solvent is evaporated by, for example, vacuum distillation and crude phenylenediamine having a purity of at least about 80 percent, typically from 85 to 90 percent, is recovered as a crystalline solid. The crude phenylenediamine may be further refined to a purity of at least about 97 percent by subjecting the crude product to, for example, vacuum sublimation.

The invention is further illustrated but is not intended to be limited by the following examples.

EXAMPLE 1

50 grams of 1,4-dichlorobenzene and 700 milliliters of aqueous 28 percent ammonium hydroxide solution containing 8.7 grams of cuprous chloride (CuCl) were charged to a 1-liter capacity Hastelloy-C Magnedrive Autoclave (available from Autoclave Engineers, Inc.). The mixture was reacted for 12 hours at a temperature of between 200° C. to 220° C. and a pressure of between 700 psig to 850 psig.

The reaction mixture was then cooled to ambient temperature and transferred to a 1-liter Erlenmeyer filtering flask. 7 grams of sodium hydrosulfite ($Na_2S_2O_4$) were added. The mixture was heated to about 50°-55° C. and aspirated for about two hours to remove unreacted ammonia.

The reaction mixture was cooled to ambient temperature and adjusted to a pH of between 12 to 13 by the addition of anhydrous sodium hydroxide pellets. The alkaline mixture was filtered to remove precipitated copper hydroxide and again aspirated to remove liberated ammonia.

The ammonia-free filtrate was transferred to an extraction flask equipped with a reflux condenser and extracted with 350 milliliters of methylene chloride for 12 hours at a temperature of 35° C. The methylene chloride phase was separated from the aqueous alkaline phase, the methylene chloride was evaporated, and about 38.3 grams of crude, solid p-phenylenediamine having a purity of 87.4 percent were recovered.

A 5 gram portion of the crude p-phenylenediamine was subjected to vacuum sublimation at a temperature of between 85° C. and 95° C. and a reduced pressure of about 1 millimeter of mercury for about 4 hours. 4.8 grams of 97.5 percent p-phenylenediamine were recovered.

EXAMPLE 2 (Comparison)

The procedure described in Example 1 was followed except that 350 milliliters of 1,1-dichloroethane was used in place of methylene chloride to extract the aqueous alkaline solution. About 29.3 grams of crude p-phenylenediamine having a purity of about 68 percent were recovered from the 1,1-dichloroethane.

Although the invention has been described with specific reference to and specific embodiments thereof, it is to be understood that it is not intended to be so limited since changes and alterations therein may be made which are within the full and intended scope of this invention as defined by the appended claims.

I claim:

1. In a process for the preparation of a solid phenylenediamine by reacting a dichlorobenzene with ammonia in the liquid phase in the presence of a copper catalyst, treating the reaction mixture with an alkali metal hydroxide to both recover the catalyst as insoluble copper hydroxide and to liberate free phenylenediamine, extracting phenylenediamine from the aqueous alkaline reaction mixture with an organic liquid and recovering solid phenylenediamine from the extracting liquid, the improvement consisting of extracting phenylenediamine from the aqueous alkaline reaction mixture by liquid-liquid extraction with a $C_1$ chlorinated solvent selected from the group consisting of methylene chloride, chloroform and carbon tetrachloride.

2. The improvement of claim 1 wherein the solvent is methylene chloride.

3. The improvement of claim 1 wherein the phenylenediamine is p-phenylenediamine.

4. The improvement of claim 1 wherein from about 20 percent to about 100 percent by volume of solvent based on the volume of aqueous alkaline reaction mixture is used for extraction.

5. The improvement of claim 1 wherein the aqueous alkaline reaction mixture is extracted at a temperature below about 100° C. and at a pressure sufficient to maintain the liquid phase.

* * * * *